Nov. 17, 1970 M. H. RAYMUNDO Plant Pat. 3,003
BOUGAINVILLEA PLANT
Filed Oct. 23, 1968
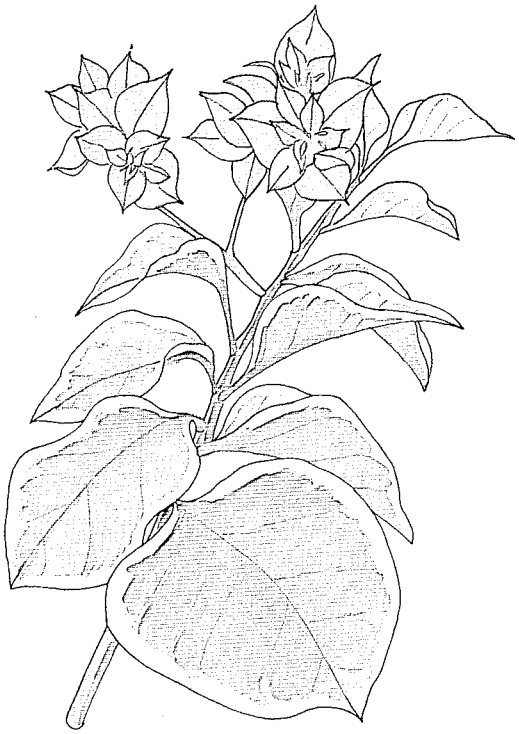
Inventor.
M. H. Raymundo
By: Robb & Robb
Attorneys.

United States Patent Office

Plant Pat. 3,003
Patented Nov. 17, 1970

3,003
BOUGAINVILLEA PLANT

Marietta H. Raymundo, Malabon, Rizal, Philippines, assignor of one-half to David Barry, Jr., trading as California Jungle Gardens, Los Angeles, Calif.

Filed Oct. 23, 1968, Ser. No. 770,132
Int. Cl. A01h 5/12
U.S. Cl. Plt.—54 1 Claim The present invention relates to a new and distinct variety of bougainvillea plant which was discovered by me as a sport in my cultivated home garden located at Iloilo City, Philippines.

At the time of my discovery aforesaid, I was growing in my garden plants of the bougainvillea variety known in the Philippines as "Mahara" (U.S. Plant Pat. No. 2,630). In the course of caring for these plants, I severely pruned the same, and as the plants continued to grow, my attention was attracted to one particular plant among the regular plantings of "Mahara" which appeared to be quite different from all the other plants of "Mahara." On close inspection of this particular plant, I found that it had produced a mutation or sport, and I thereupon carefully preserved the sport, kept it under close observation, and in due course, I asexually reproduced the same by cuttings taken from the sport and grown by me in my garden aforementioned. Continued observations of the sport and the progeny thereof derived from the cuttings aforesaid, have convinced me that it comes true and is established through succeeding propagations and is a new variety which is distinguished from its parent, as well as from all other bougainvillea varieties of which I am aware, as evidenced by the following unique combination of characteristics which are outstanding therein:

(1) A habit of growth, bract structure and bract color substantially identical to the parent variety "Mahara"; and (2) Distinctive, attractive and marginally variegated leaves, said leaves being pinkish in color along both sides of the leaf margins when young, with the color corresponding to Light Rosolane Purple (Ridgway), but fading to white with age, and creating an interesting and pleasing delineation of the plant leafage which is unique to the genus Bougainvillea, as illustrated in the accompanying drawing.

The drawing also illustrates the multiple bract structure and color, as typical of the new variety, with the bracts, in lieu of flowers, being borne in sets of three which diminish in size and giving the bract clusters a tufted appearance. Even without bracts, the variegated leaf pattern is highly ornamental and enhances the attractiveness of the plant at all times.

Since my new variety substantially corresponds to the patented variety "Mahara," except for the variegated leaf color pattern, reference can be conveniently made to Plant Pat. No. 2,630 aforementioned for a more detailed description of the general features, and therefore these details need not be described herein.

I claim:

1. A new and distinct variety of bougainvillea plant, substantially as herein shown and described, characterized particularly as to novelty by the unique combination of a habit of growth, bract structure and bract color substantially identical to the parent variety "Mahara," and distinctive, attractive and marginally variegated leaves, said leaves being pinkish in color along both sides of the leaf margins when young, with the color corresponding to Light Rosolane Purple (Ridgway), but fading to white with age, and creating an interesting and pleasing delineation of the plant leafage which is unique to the genus Bougainvillea, as illustrated in the accompanying drawing.

No references cited.

ROBERT E. BAGWILL, Primary Examiner